(12) United States Patent
Karlsson

(10) Patent No.: US 7,112,187 B2
(45) Date of Patent: Sep. 26, 2006

(54) INJECTING DEVICE

(75) Inventor: Anders Karlsson, Saltsjo-Boo (SE)

(73) Assignee: SHL Medical AB, Nacka (SE)

( * ) Notice: Subject to any disclaimer, the term of this patent is extended or adjusted under 35 U.S.C. 154(b) by 219 days.

(21) Appl. No.: 10/669,053

(22) Filed: Sep. 24, 2003

(65) Prior Publication Data

US 2005/0261634 A1   Nov. 24, 2005

Related U.S. Application Data

(60) Provisional application No. 60/412,815, filed on Sep. 24, 2002.

(51) Int. Cl.
*A61M 5/00* (2006.01)
(52) U.S. Cl. .................................. 604/187; 604/246
(58) Field of Classification Search ............. 604/187, 604/246
See application file for complete search history.

(56) References Cited

U.S. PATENT DOCUMENTS

| | | | | |
|---|---|---|---|---|
| 4,710,178 A * | 12/1987 | Henri et al. | ................ | 604/209 |
| 5,112,317 A * | 5/1992 | Michel | ................ | 604/208 |
| 5,226,896 A * | 7/1993 | Harris | ................ | 604/211 |
| 5,378,233 A * | 1/1995 | Haber et al. | ................ | 604/83 |
| 5,514,097 A * | 5/1996 | Knauer | ................ | 604/136 |
| 5,634,906 A * | 6/1997 | Haber et al. | ................ | 604/136 |
| 6,096,010 A * | 8/2000 | Walters et al. | ................ | 604/207 |
| 6,099,503 A | 8/2000 | Stradella | | |
| 6,221,046 B1 | 4/2001 | Burroughs et al. | | |
| 6,221,053 B1 * | 4/2001 | Walters et al. | ................ | 604/211 |
| 2001/0037087 A1 | 11/2001 | Knauer | | |
| 2004/0186442 A1 * | 9/2004 | Graf et al. | ................ | 604/207 |

FOREIGN PATENT DOCUMENTS

| EP | 0 554 996 | 8/1993 |
|---|---|---|
| EP | 554995 A1 * | 8/1993 |
| WO | WO 92/19296 | 11/1992 |

* cited by examiner

*Primary Examiner*—Nicholas D. Lucchesi
*Assistant Examiner*—Laura Bouchelle
(74) *Attorney, Agent, or Firm*—Young & Thompson

(57) ABSTRACT

An injection device having an elongated body, including a container with medicament, elements for connecting a needle to the container, actuating elements capable of injecting a dose of medicament upon activation, activating elements capable of activating the actuating elements, a needle shield arranged to the body and slidable between an extended and a retracted position in relation to the body. The needle shield is designed and arranged such that, upon penetration of the needle into a patient, when moved to its retracted position, acts on the activating elements, which in turn activates the actuating elements and injects a dose.

16 Claims, 20 Drawing Sheets

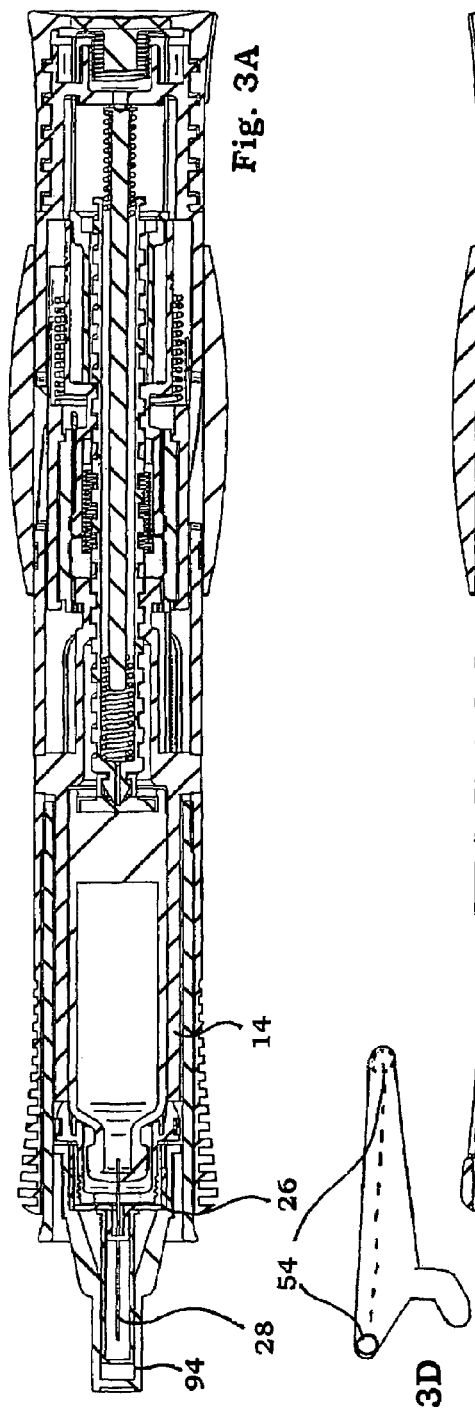
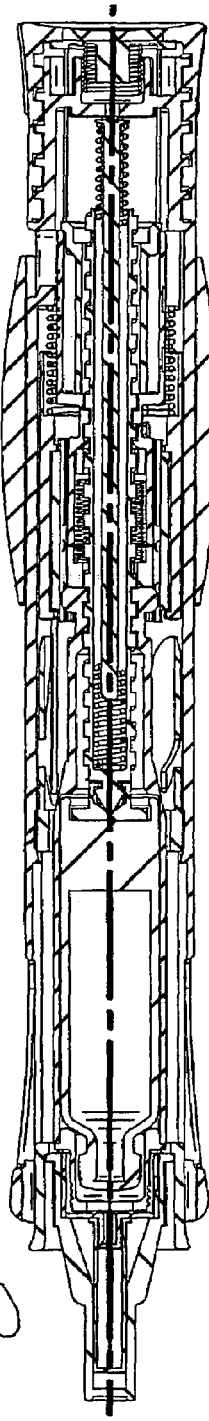
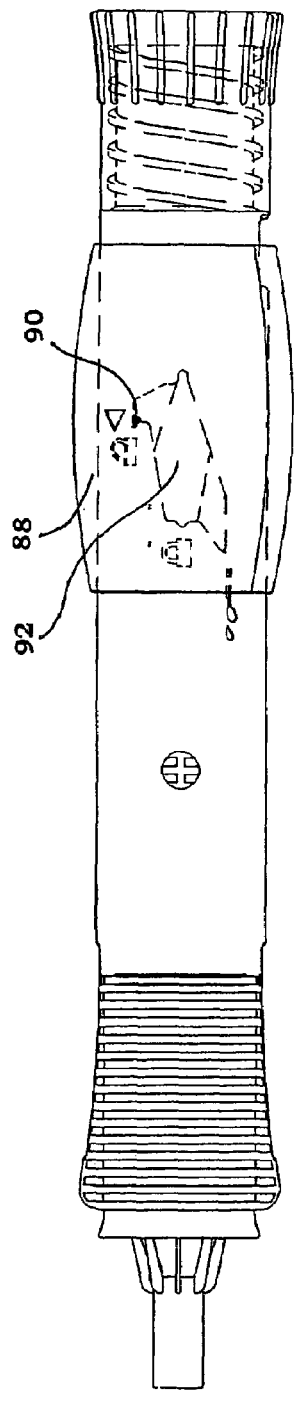
Fig. 3A  Fig. 3B  Fig. 3C  Fig. 3D

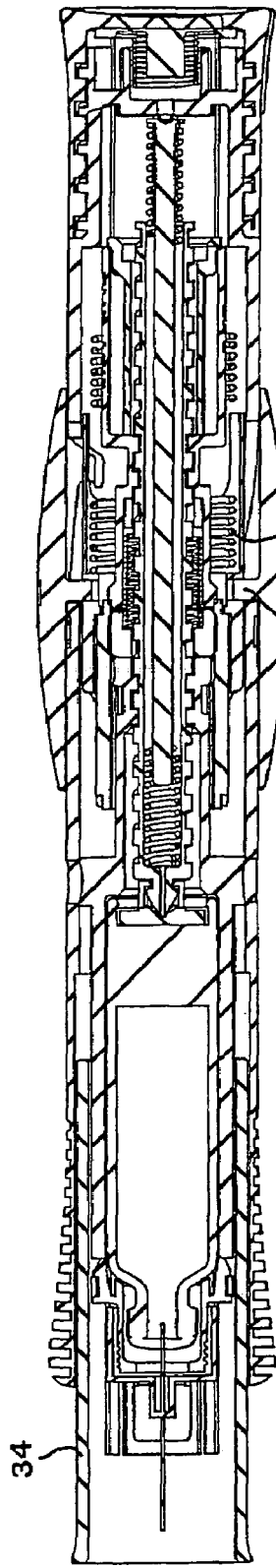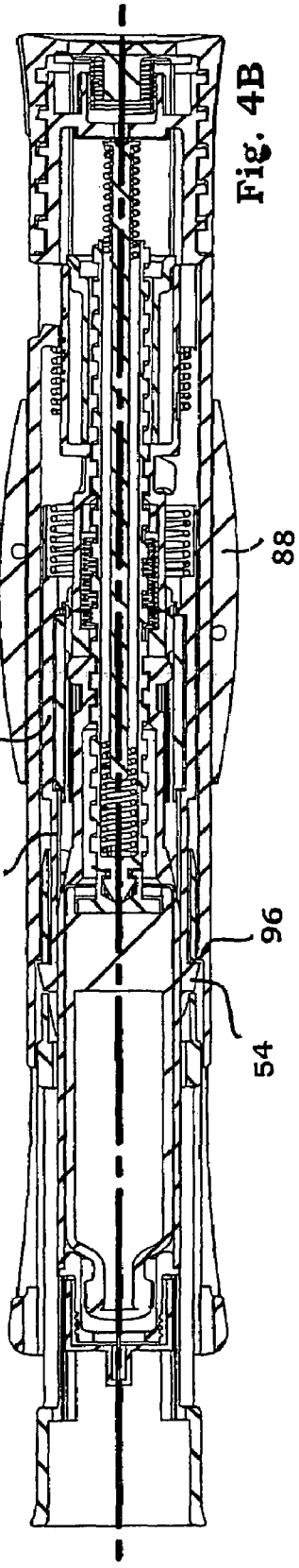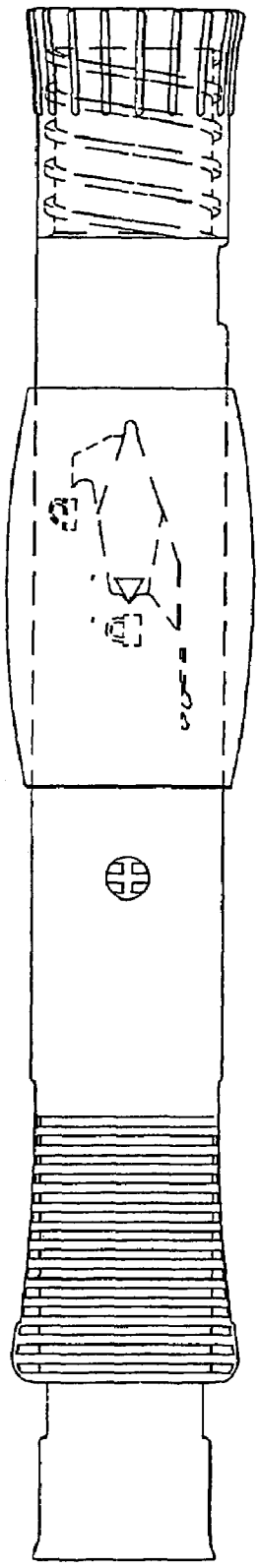

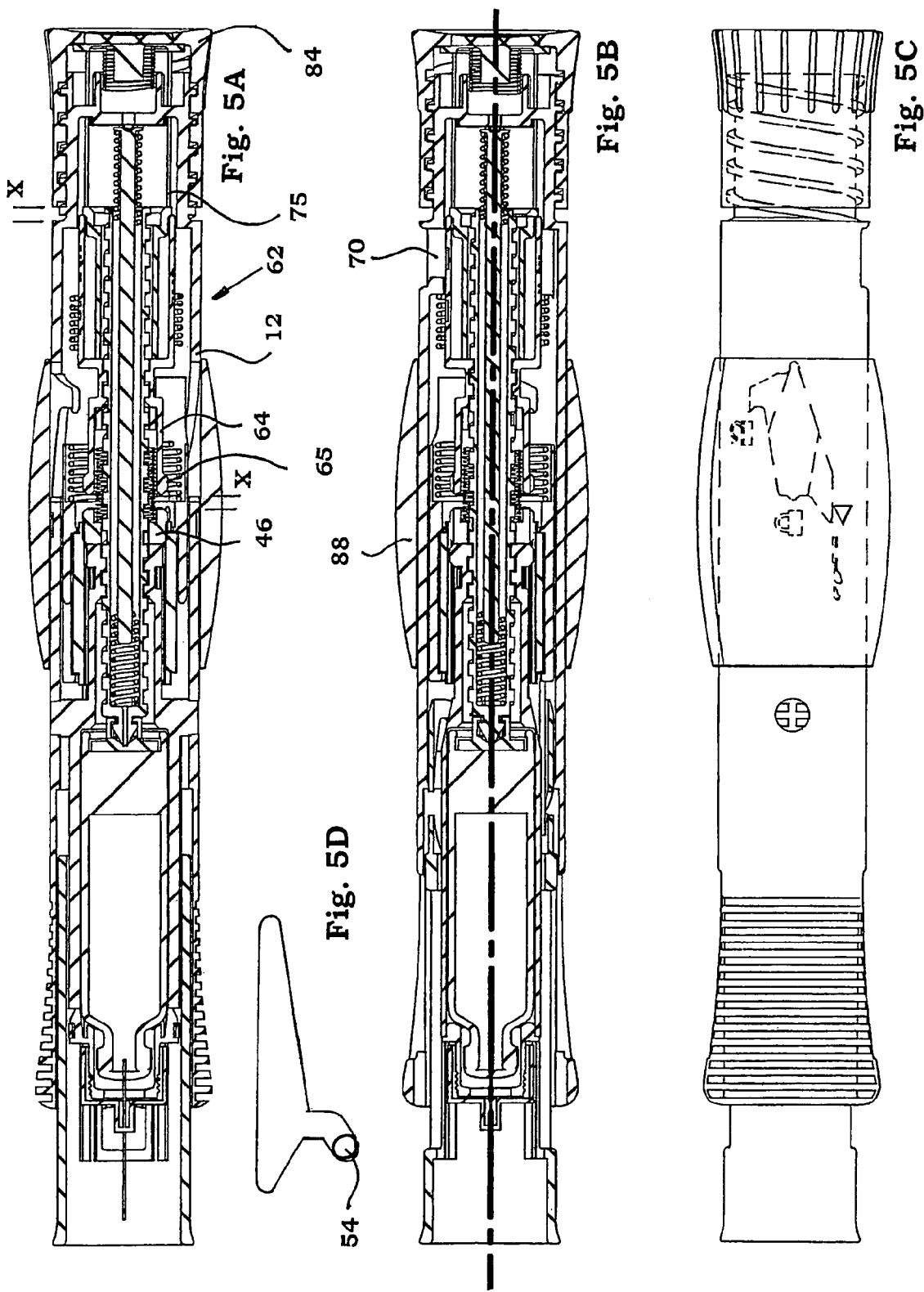

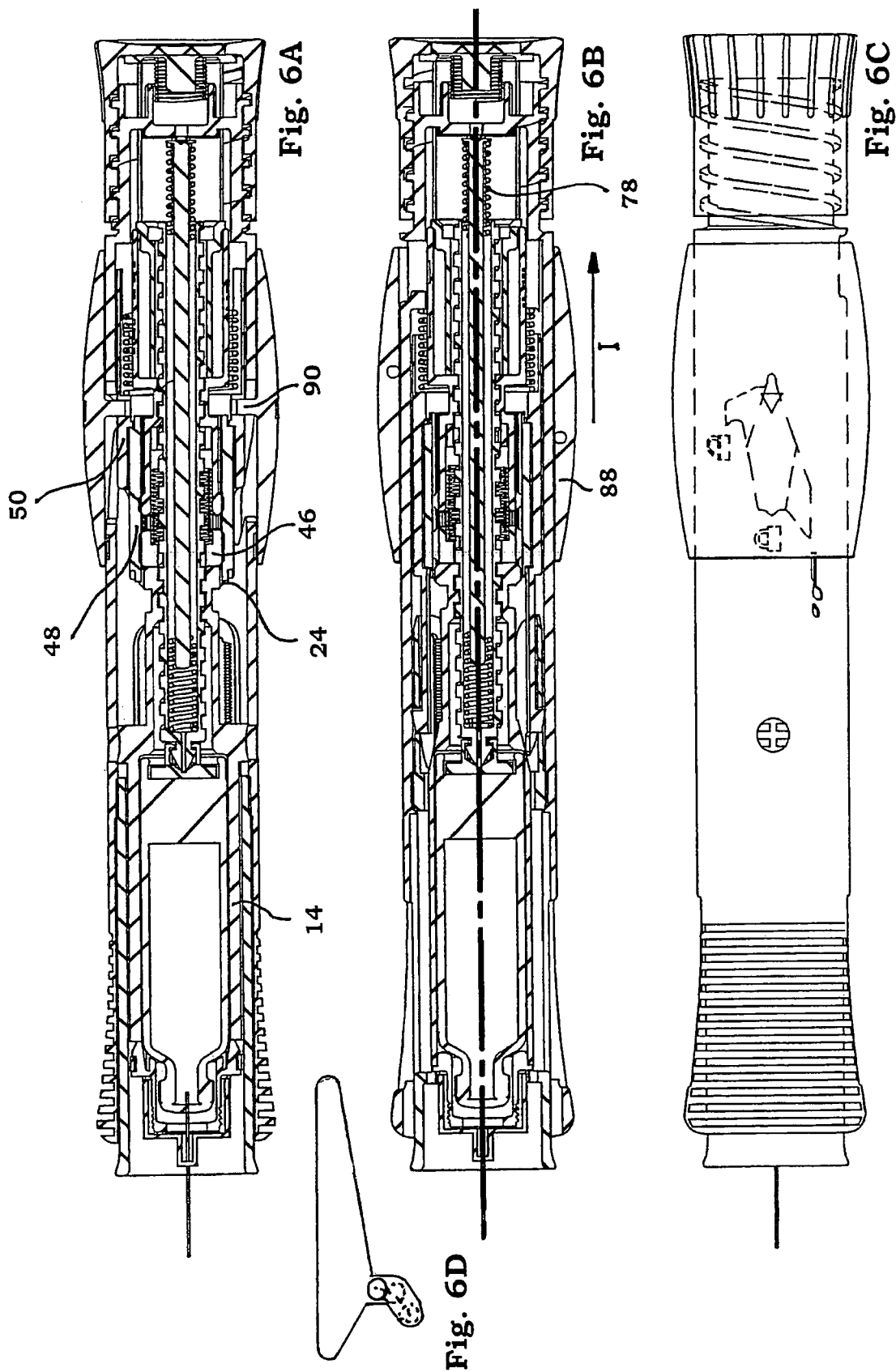

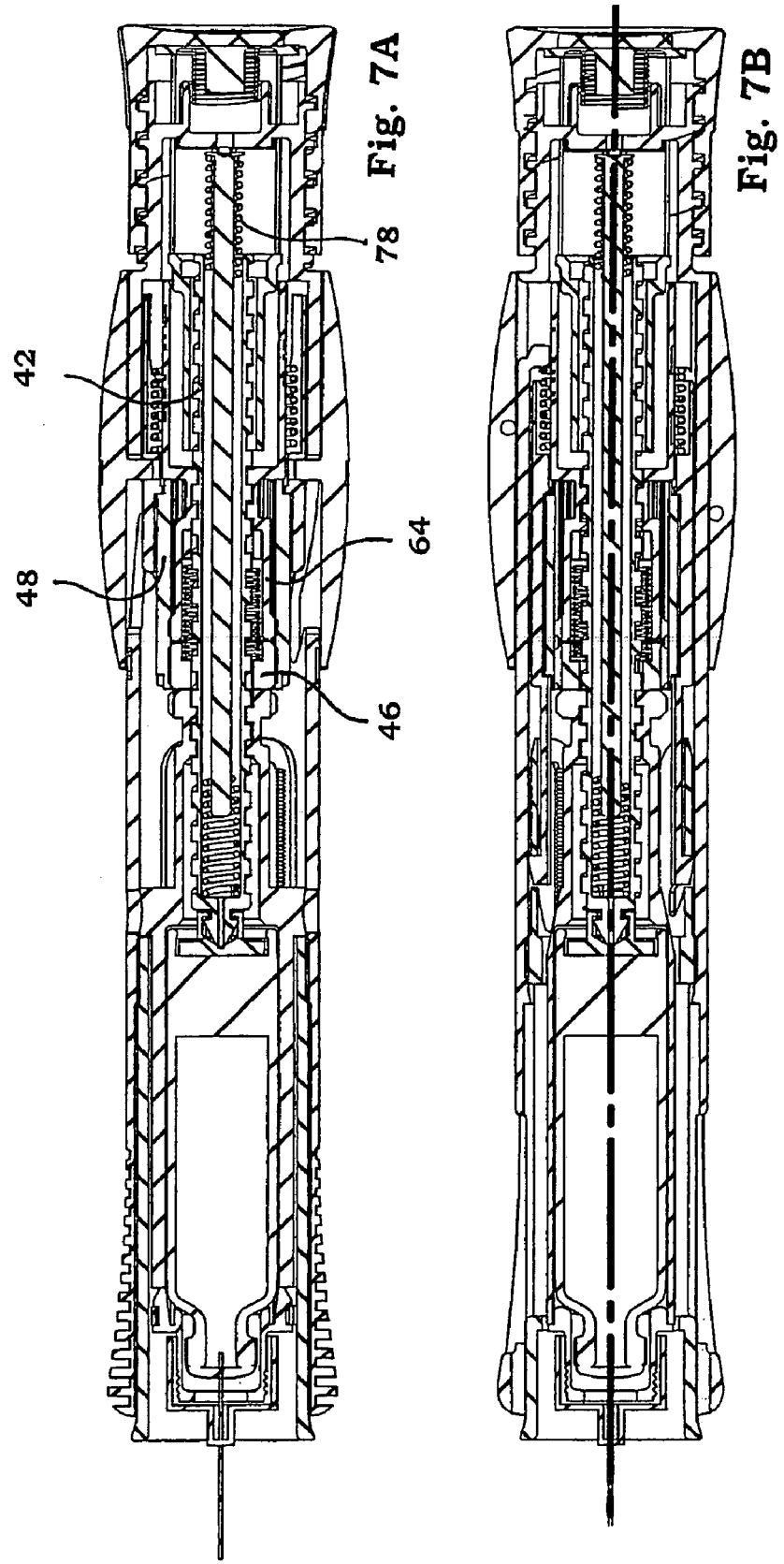

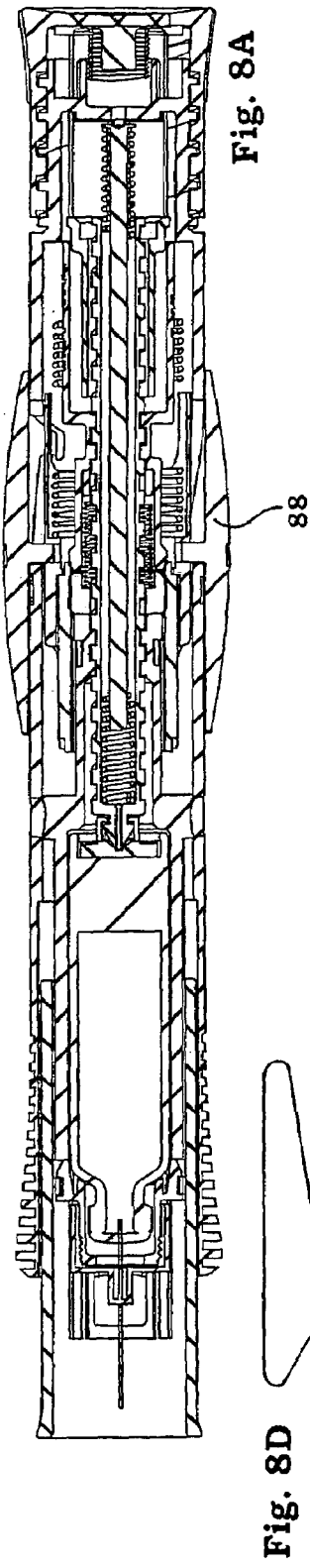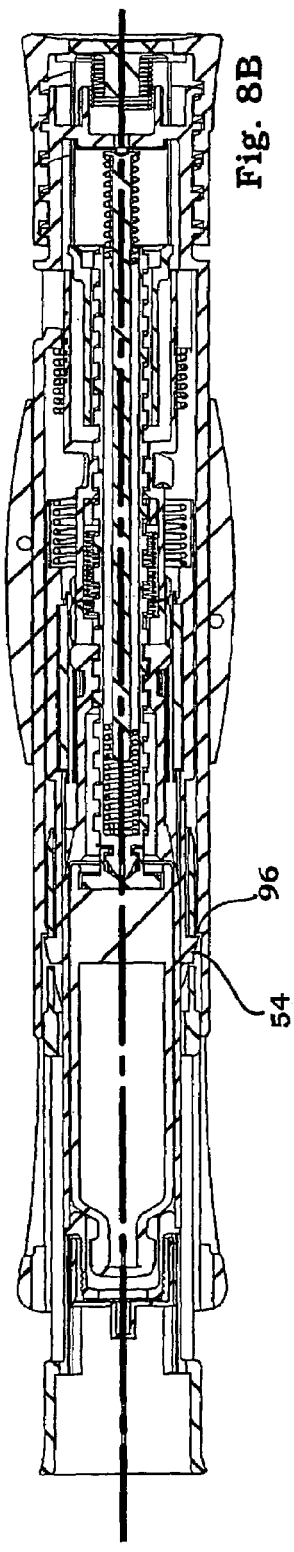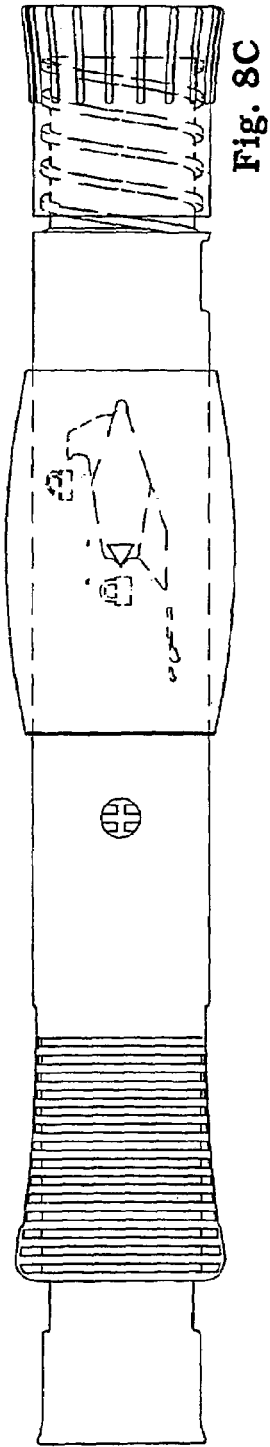

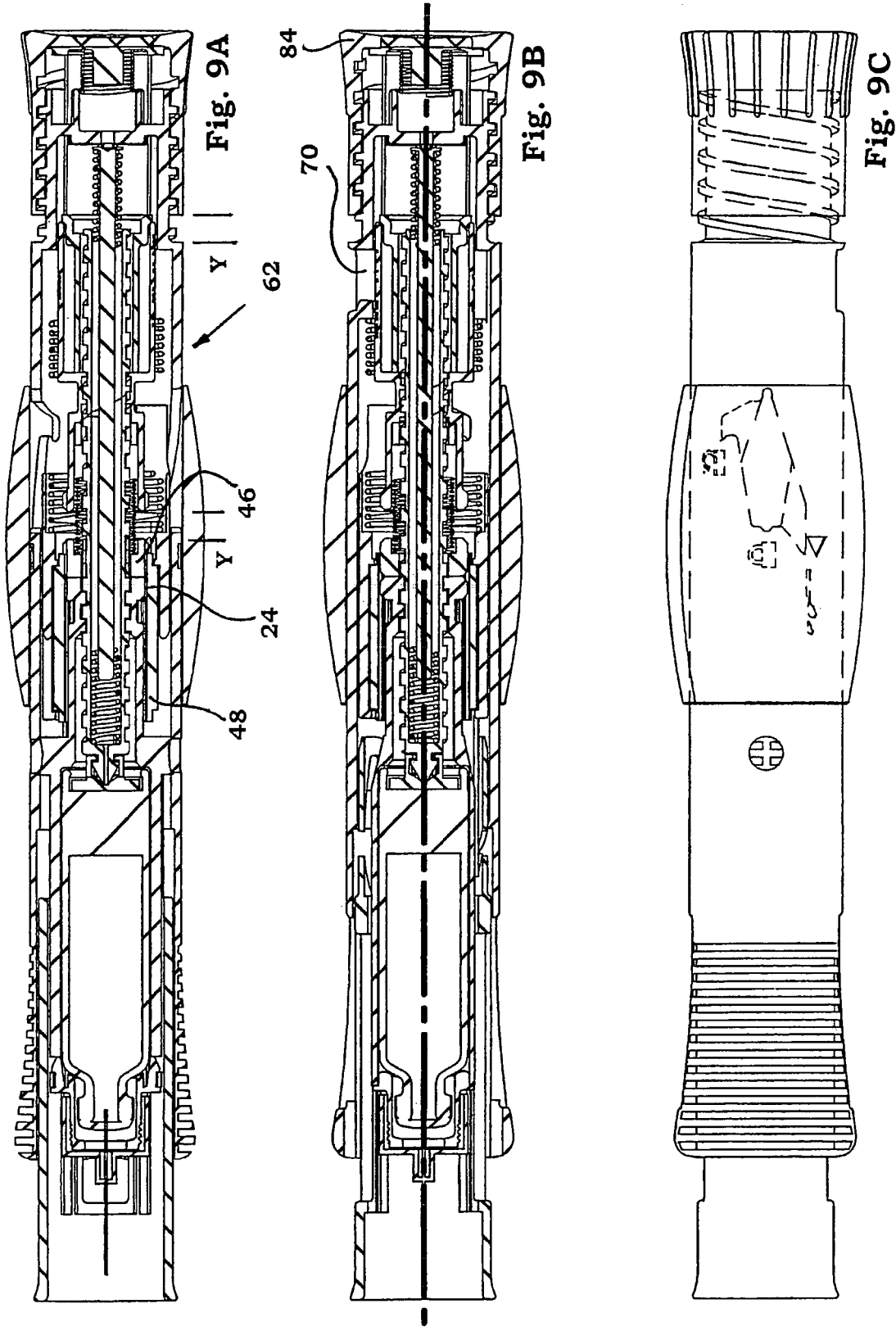

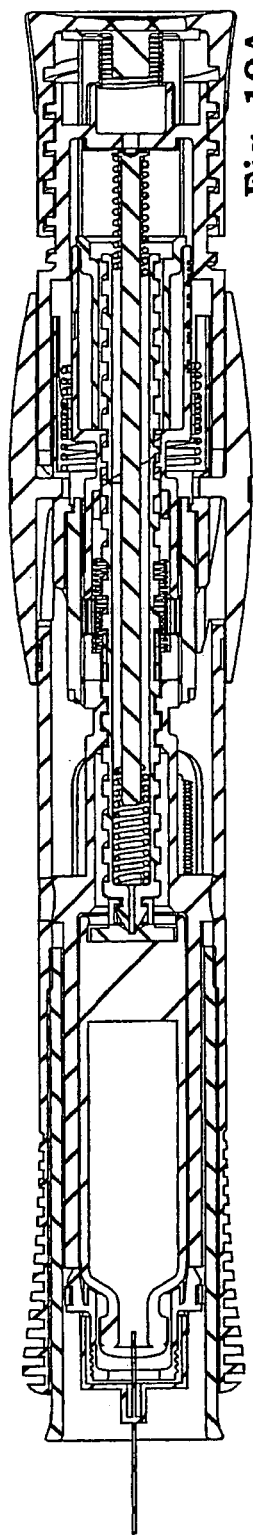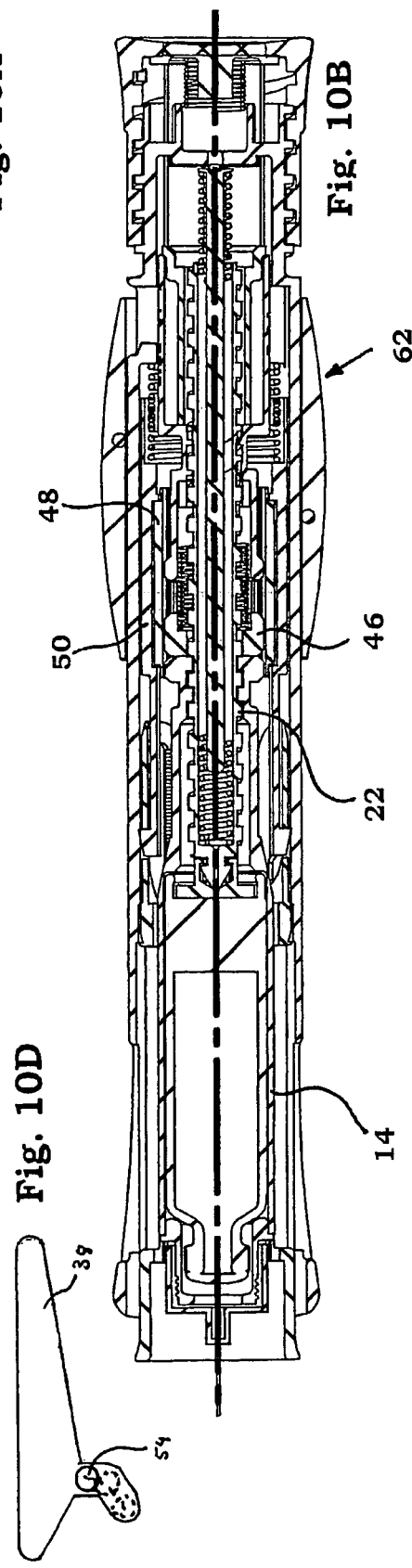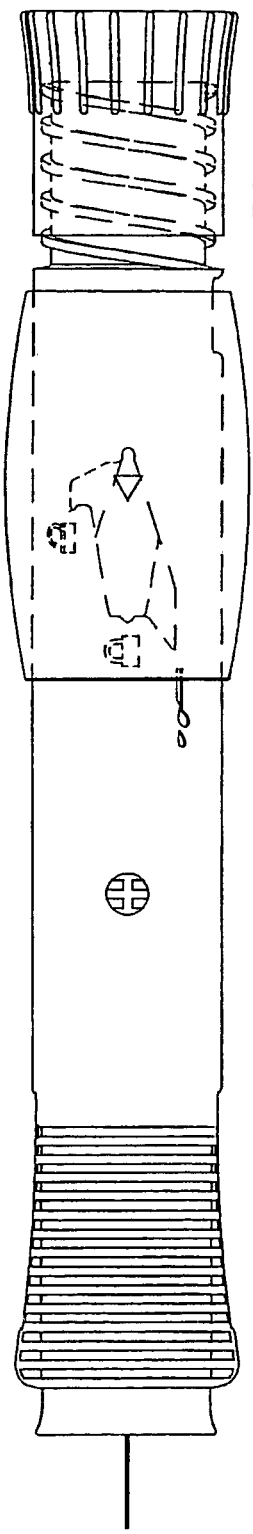
Fig. 10A
Fig. 10B
Fig. 10C
Fig. 10D

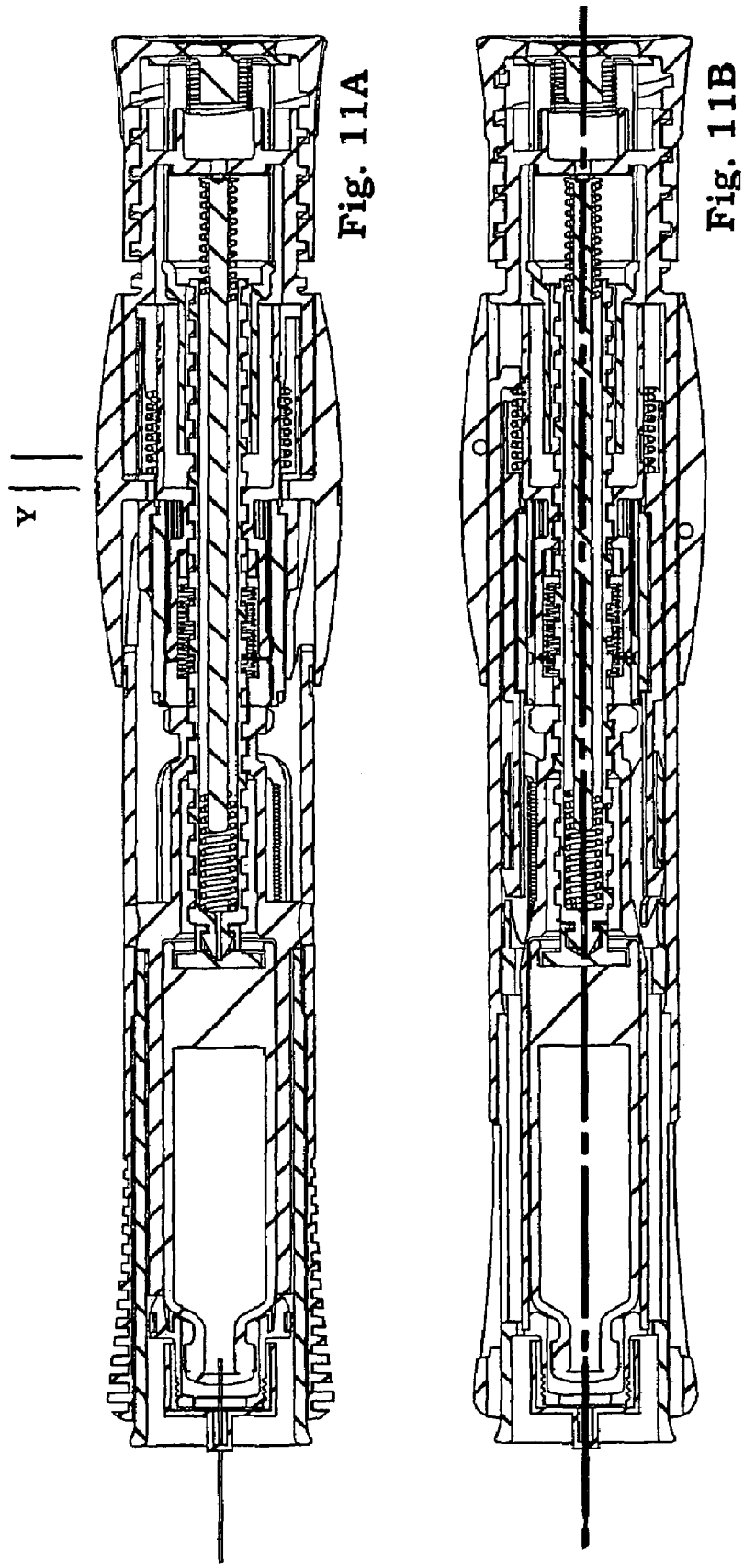

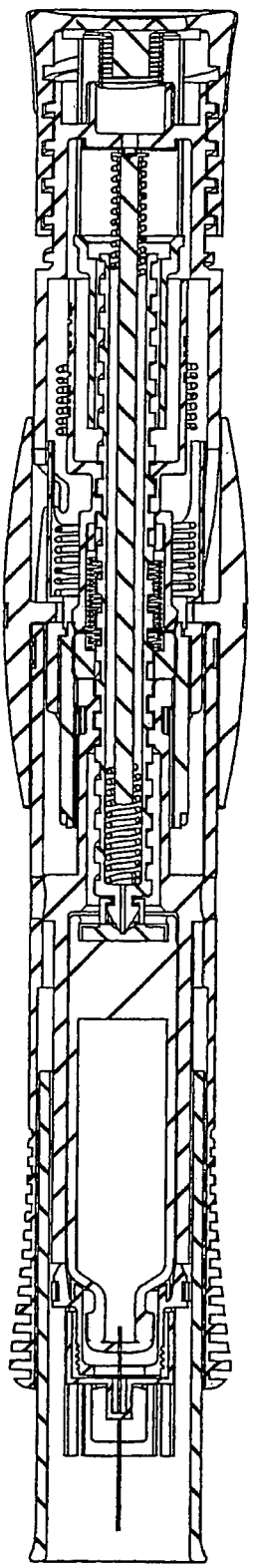
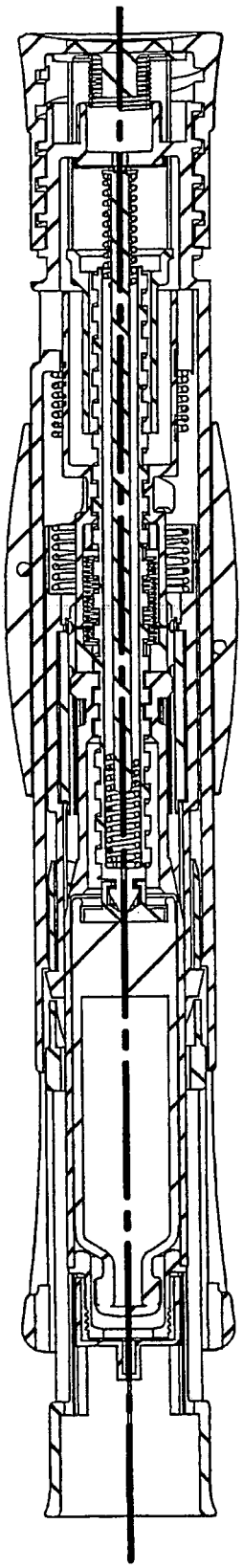
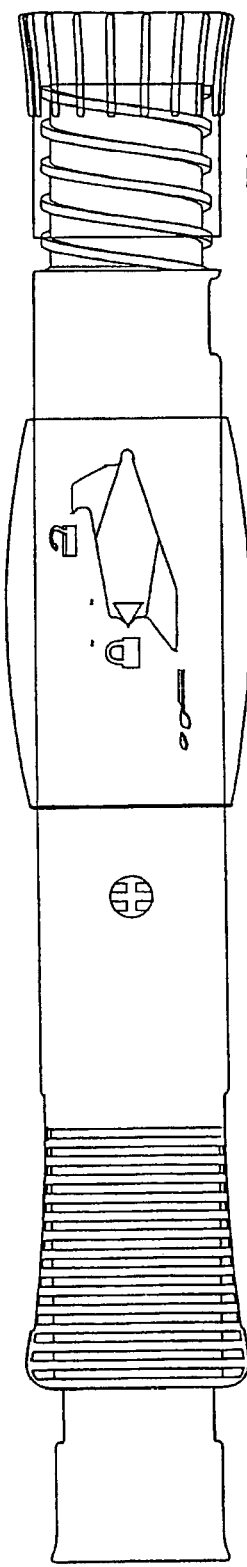
Fig. 12A
Fig. 12B
Fig. 12C

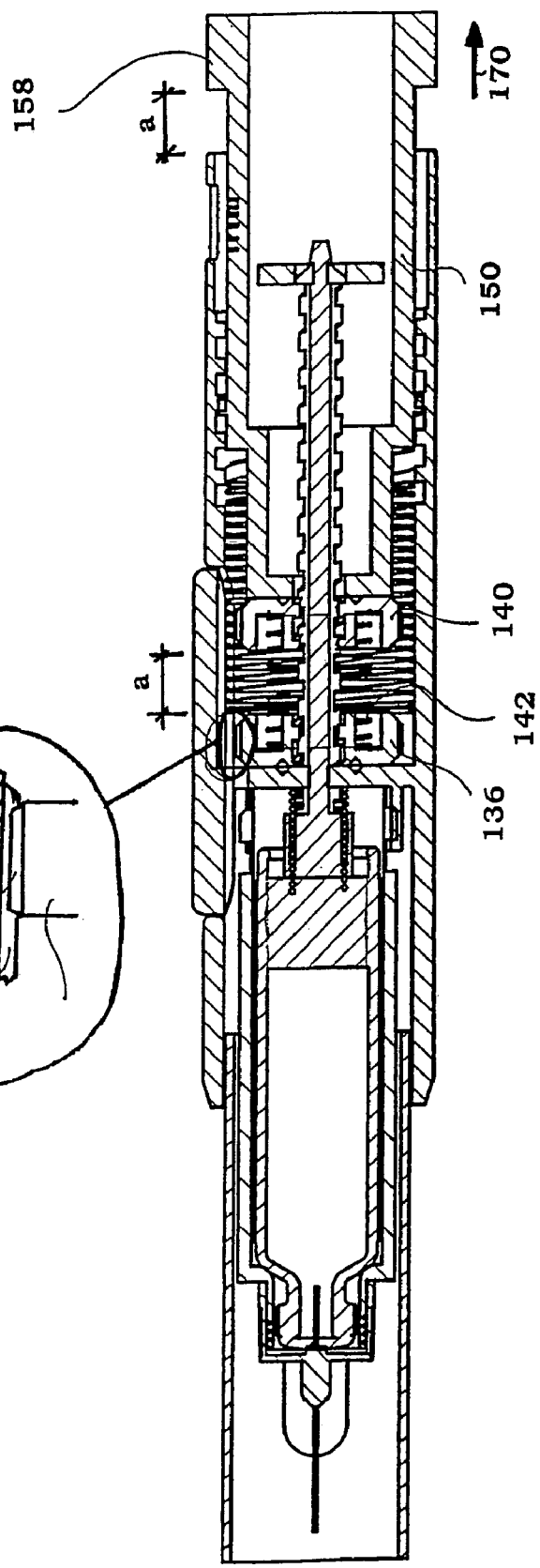
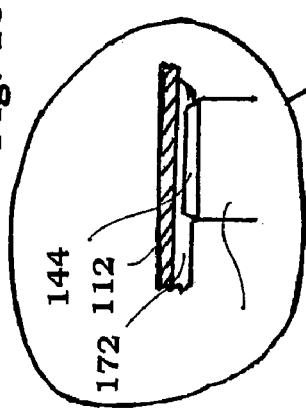
Fig. 15B
Fig. 15A

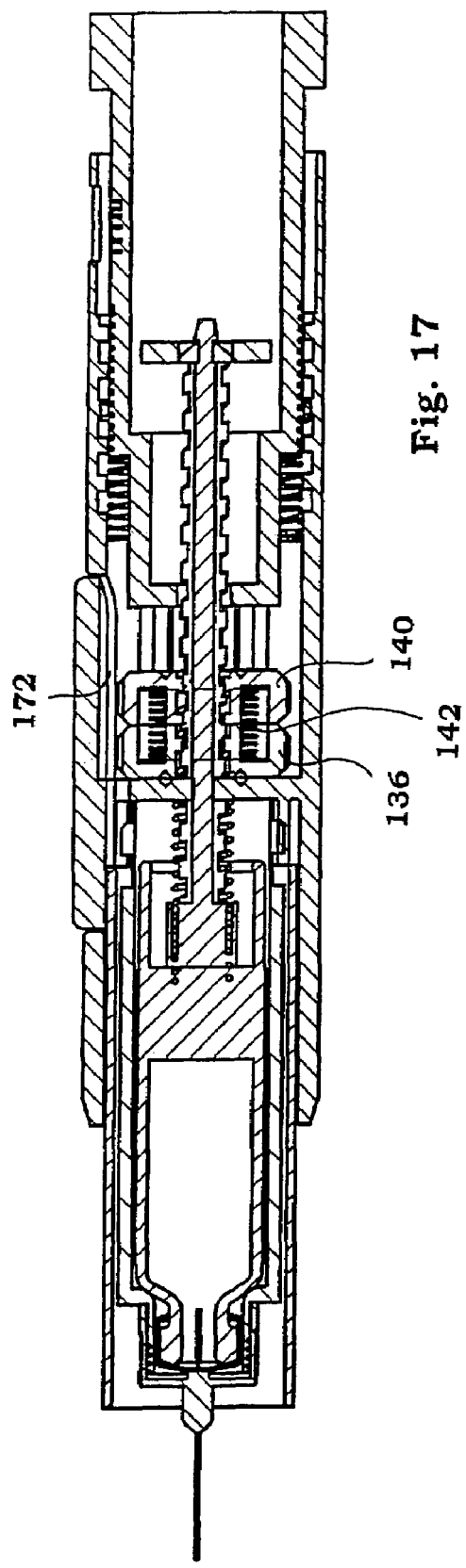

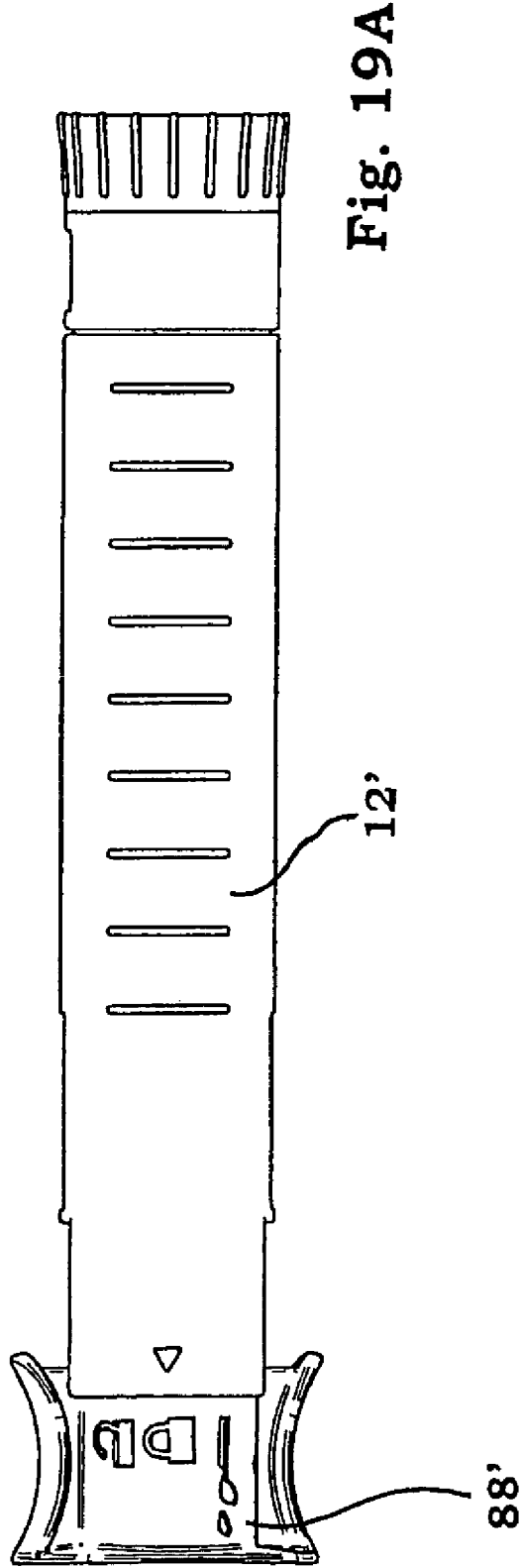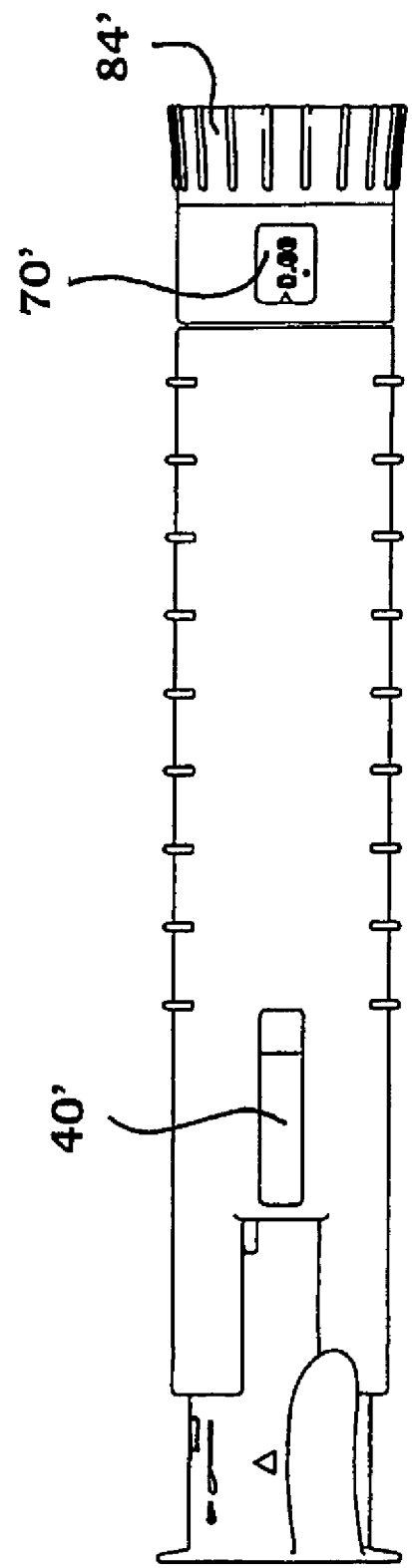

INJECTING DEVICE

TECHNICAL FIELD

The present invention relates to an injector for delivery of medication to a patient and more specifically to an injector which is capable of delivering a variable dose in a convenient way.

BACKGROUND OF THE INVENTION

Injectors are used more and more for delivery of medication to patients, and they are particularly useful when they are handled by the patients themselves. In order to facilitate the handling the injectors should be easy to handle with a certain degree of automatic functions, they should be reliable and obvious to the user in order to avoid erroneous use. The injectors should further be provided with safety means to prevent accidental needle sticks from used needles due to the contamination hazards.

One type of injector on the market is the so called pen injector, a rather slim fountain pen-like injector. It is either designed so that the needle is penetrated into the skin manually by the user and subsequently the user presses a button, usually on top of the injector in order to inject the medicament, or that the needle is penetrated automatically and the medicament is injected when the button is pressed.

A drawback with the latter type of injector is that the mechanism becomes rather complicated in order to obtain that degree of automation, and therefore rather costly and also that it becomes difficult to obtain a really pen-like size. On the other hand, a drawback with the first type of injector is that there might be a problem handling the injector in that the needle first has to be pushed into the body, whereby this category of patients tends to hold the injector in a sort of stabbing manner. Subsequently, for injecting the medicament, they have to change grip in order to reach and depress the activating button, which may lead to erroneous or even no injection and certainly a degree of discomfort because of bending/moving the needle during the change of grip and/or that the patient needs to use both hands in order to operate the device.

In the field of injectors there is more and more a need for the possibility of delivering a plurality of doses of medicament. Many new drugs are to be delivered in very small quantities, and these small quantities are difficult to package in one-dose containers and inject from the containers. A few solutions to this has been presented where a larger container is emptied in steps. In order to have a reasonable accuracy as regards the repetitive and accurate quantity of the delivered doses, rather complex mechanisms have been developed. In order to repeat the dose, many injectors require their power supplier to be reloaded, which requires additional handling steps that require force by the user.

A further problem associated with injecting devices capable of delivering multiple doses is how to handle the last dose. There is often a problem if a last dose remaining in the medicament container is smaller than the dose quantity required or set.

BRIEF DESCRIPTION OF THE INVENTION

The aim of the present invention is to provide an injector that has a relatively small size, that is easy to use even for weak persons and children in a sort of "one hand, one manoeuvre"—functionality and that provides additional possibilities for multiple dose delivery in a reliable, repetitive and safe way.

The aim is obtained by the features of claim 1. Further advantageous aspects and features of the invention are defined by the dependent claims.

According to a main aspect of the invention it is characterised by an injection device comprising an elongated body, including a container with medicament, means for connecting a needle to the container, actuating means capable of injecting a dose of medicament upon activation, activating means capable of activating said actuating means, a needle shield arranged to said body and slidable between an extended and a retracted position in relation to said body, characterised in that said needle shield is designed and arranged such that, upon penetration of the needle into a patient, when moved to its retracted position, acts on said activating means, which in turn activates said actuating means and injects a dose.

One main advantage with the present invention is that it is very easy and simple to use, even for weak patients and children with a minimum of operating steps and yet with a high degree of automation contained in a fairly compact injector. The simplicity of use is very much characterised in that the user only has to hold the device in one single way in order to penetrate and inject, ie. use only one hand without changing grip in order to have one manoeuvre.

A further advantage is that the injector can provide a high degree of precision in delivery of the set dose and that the dose can be set at different dose quantities down to increments of 0,01 ml with a compact, reliable and repetitive design. This enables the patient to alter the injected quantity, for instance as required by the physician, following a certain treatment plan. The design of the dose varying device of the injector is however such that a dose quantity set for an injection becomes the "default" quantity for any subsequent injections until the patient manually alters it. This further enhances the ease of use in that the patient does not have to set a certain dose for each injection.

The device according to the invention is also able to take care of the problem of the last dose remaining in the medicament container in that the device cannot indicate, or be set to, more than the remaining quantity in the container. This ensures that the patient is aware of the remaining amount when the last dose is to be delivered, thus ensuring that the patient does not run the risk of injecting a dose that is smaller, and perhaps insufficient, than the required and prescribed dose without being informed and hence not being able to cope with the insufficient dose and correcting this by a subsequent dose.

A yet further advantage with the injector of the invention resides in the preloaded actuating spring when the injector is delivered to the patient. The preload of the actuating spring is sufficient to empty the medicament container through a number of doses. Thus, the patient does not have to preload nor reload the actuating spring for each injection.

These and other aspects of and advantages with the present invention will become apparent from the following detailed description of embodiments of the invention and from the accompanying drawings.

BRIEF DESCRIPTION OF THE DRAWINGS

In the following detailed description of the invention reference will be made to the accompanying drawings, of which FIGS. 14–18 show the injector according to FIG. 13 in different positions during the use of the injector, FIGS. 19A–B show a variant of the embodiment of FIGS. 1–12.

DETAILED DESCRIPTION OF THE INVENTION

Figure 1A:
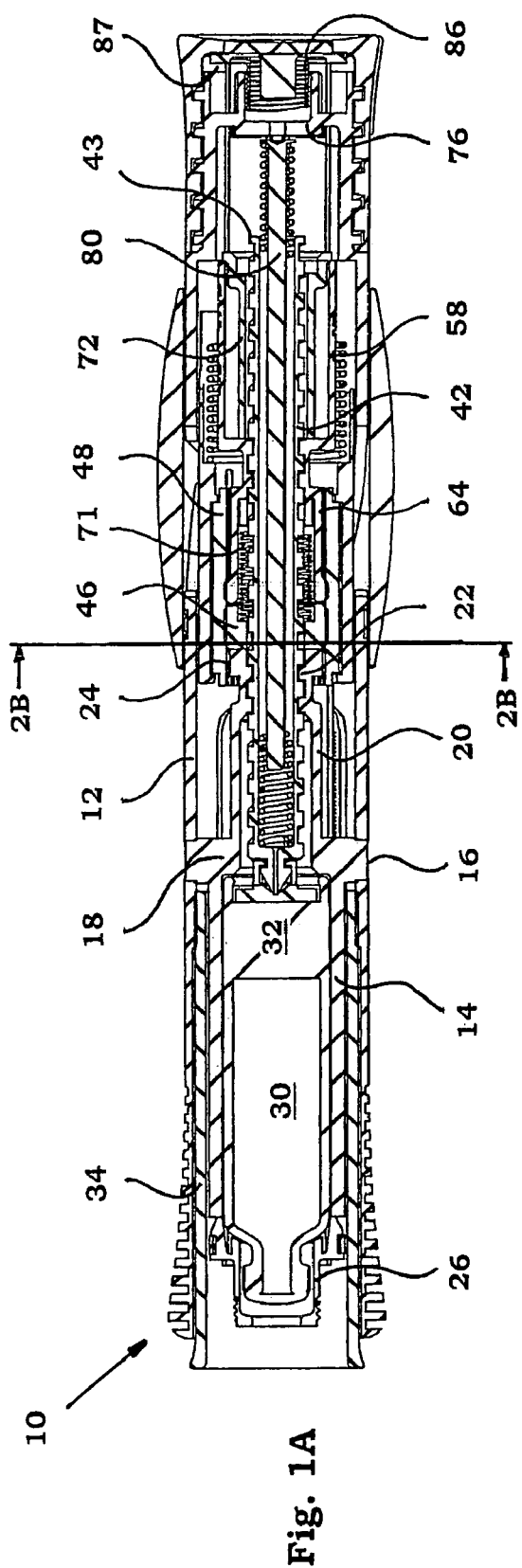
FIGS. 1A–B are longitudinal cross-sectional view of a first embodiment injector according to the invention where the view 1B is taken 90° in relation to 1A.
Figure 1B:
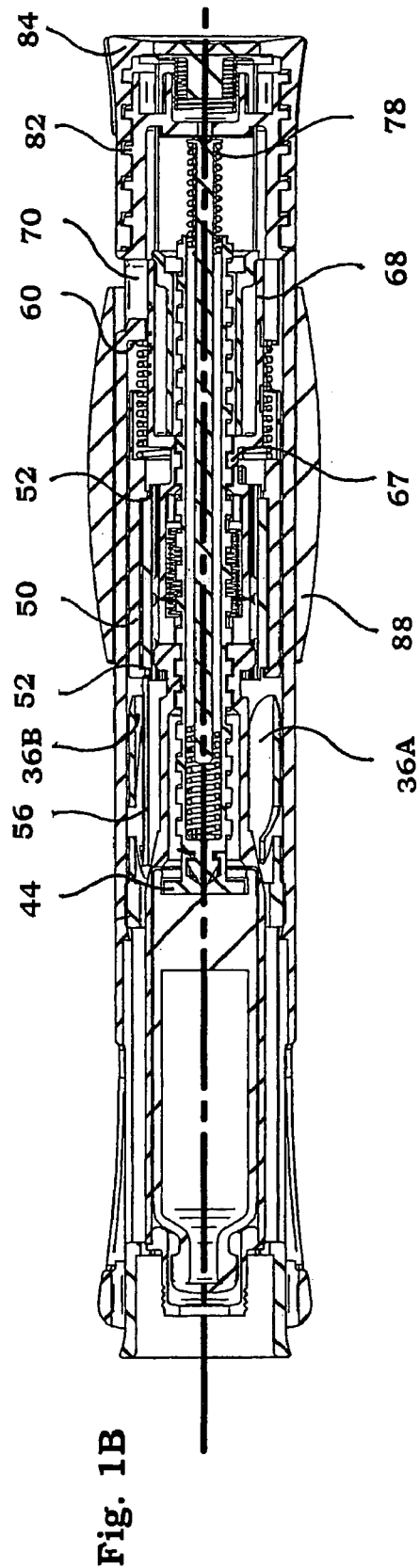

A first embodiment of the injector according to the invention shown in FIG. 1 is generally denoted with reference numeral 10. In the following detailed description reference will be made to the front or forward end or direction which corresponds to the end of the device where an injection needle is arranged and thus the rear or rearward end is the opposite end of the device.

Figure 2A:
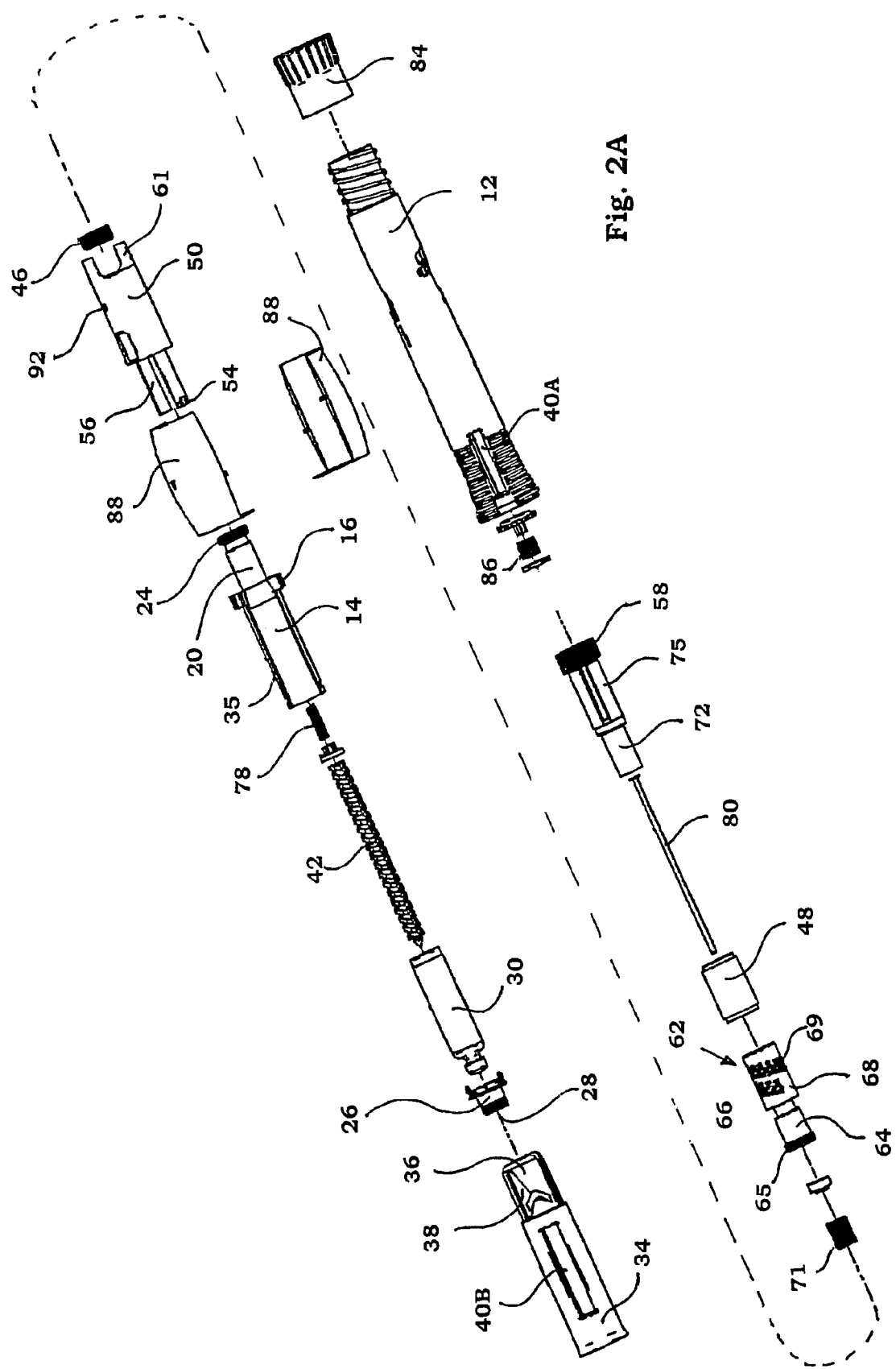
FIG. 2A is an exploded view of the embodiment shown in FIG. 1.

It comprises a generally tubular main housing 12 open at the front (to the left in the figures, and rear ends. Adjacent the front end a generally tubular container holding housing 14 is arranged. It is secured to the main housing by protrusions 16 extending through recesses in the main housing. The rear part of the container holding housing is further provided with a wall 18 having a centrally positioned through-hole. From the wall a generally tubular section 20 is extending rearwardly and arranged with threads 22 on the inner surface adjacent its end. The outer surface at the end is arranged with longitudinally extending grooves or splines 24 around its circumference. At the front end of the container holding housing 14 a threaded neck portion 26 is attached, having an opening in the front direction, for attaching a needle 28, as shown in FIG. 3. Inside the container holding housing a container 30 is arranged, containing the medicament to be injected into a patient. The rear part of the container is arranged with a slidable piston 32. Between the main housing and the container holding housing a needle shield 34 is arranged slidably between a retracted state and an extended state, as will be explained below. The needle shield 34 is however fixed rotationally in that the outer surface of the container holding housing is arranged with longitudinally extending ridges 35, FIG. 2A, and that the inner surface of the needle shield is arranged with longitudinally extending grooves having corresponding dimensions as the ridges. The rear end of the needle shield is arranged with two tongues 36A, B, FIG. 1B, each having a cut-out groove 38, with a certain shape. Both the main housing and the needle shield are provided with windows 40A and 40B respectively, and the container holding housing 14 is preferably made of a clear material in order for the patient to be able to view the container and its content.

A threaded drive rod 42 is in engagement with the threads 22 of the rear section 20 of the container holding housing, passes through the wall 18 and is in contact with the piston 32 of the container. Preferably an abutment plate 44 is arranged between the piston and the drive rod where the abutment plate is arranged with a recess and the end of the piston is pointed and positioned in the recess so as to reduce the friction between them, as will be explained below. The opposite end of the drive rod is arranged with a stop means 43 in the form of a rim or the like, the function of which will be explained below. The length of the drive rod is also adjusted for the stroke of the piston in the medicament container.

Figure 2B:
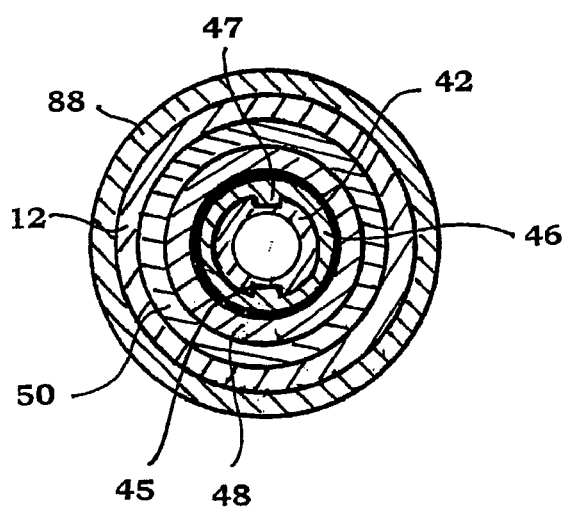
FIG. 2B is a cross-sectional view taken along the line 2B—2B of FIG. 1A, FIGS. 3–12 A–C show the injector according to FIG. 1 in different positions during the use of the injector where the B views are taken 90° in relation to the A views, where C is a side view corresponding to A.

A nut 46, hereafter named lock nut, is further also arranged on the drive rod, so as to be slidable but rotationally fixed in relation to the drive rod by means of longitudinal grooves 45 on the drive rod 42 and corresponding tabs or protrusions 47 on the inner surface of the lock nut, FIG. 2B. The outer surface of the lock nut 46 is arranged with longitudinally directed grooves or splines in the same manner as the rear end 20 of the container holding housing 14. These grooves or splines are arranged such that they may engage mating longitudinal grooves or splines arranged on the inner surface of a sleeve 48, hereafter named lock sleeve, slidably arranged outside the rear section and the lock nut. Outside and surrounding the lock sleeve 48 is a further sleeve 50, hereafter named dose actuating sleeve, arranged slidable and turnable within the main housing. The inner surface of the dose actuating sleeve is arranged with abutment ledges 52 to hold the lock sleeve 48 in a fixed longitudinal relation to the dose actuating sleeve but permitting turning of the dose actuating sleeve without turning the lock sleeve. The rear end of the needle shield is attached to the dose actuating sleeve by protrusions 54, FIGS. 2A and 4B, arranged on forwardly directed tongues 56 of the actuating sleeve 50 fitting into the recesses 38 in the tongues of the needle shield. A spring 56 is arranged between an abutment surface 58 arranged inside the dose actuating sleeve and a ledge 60 arranged on the inner surface of the main housing. The rear end of the dose actuating sleeve is arranged with two tongues 61, FIG. 2.

Along the drive rod 42 a dose adjusting means 62, hereafter named dose nut, is arranged. It comprises a first inner section 64 of generally tubular shape where its front end is arranged with longitudinally extending grooves or splines 65 in the same manner as the lock nut 46. The first section merges into a second section 66 having threads 67 on its inner surface in engagement with the threaded drive rod. The dose nut then continues into a third wider tubular section 68 with an open end. The outer surface of the third section is arranged with symbols and/or indications 69 of the mode of operation of the device as well as dose quantities to be delivered, as will be explained below. These symbols and indications are visible through a window 70 in the main housing. A spring 71 is arranged between an end surface of the lock nut 46 and an interior ledge of the dose nut 62. Inside the third section a further generally tubular sleeve 72, hereafter named dose pusher, is arranged. The rear end of the dose pusher is arranged with rearwardly extending tongues 75. The rear end of the main housing is arranged with an end wall 76 having openings (not shown) through which the tongues 75 of the dose pusher extend, thereby fixating the dose pusher rotationally with the main housing.

An actuating spring 78 is arranged inside the threaded piston extending between an abutment surface inside the front end of the piston and the end wall 76 of the main housing. A guide rod 80 is arranged inside the spring. On the outer surface of the rear end of the main housing are arranged threads 82, which cooperate with internal threads of a dose setting knob 84 arranged at the rear end of the device, to the right in the figures. A spring 86 is arranged between the inner surface of the dose setting knob and the end wall 76 of the main housing. The rear end surfaces of the tongues 75 of the dose pusher is in contact with washer 87 arranged inside the dose setting knob 84 but rotationally fixed in relation to the dose setting knob. Opposite facing surfaces of the washer and the dose setting knob are arranged with ratchets or the like in order to create distinct positions of the dose setting knob.

Outside the main housing a sleeve 88, hereafter named mode selector, is arranged slidably and turnable. The inner surface of the mode selector is arranged with two inwardly directed pins or protrusions 90, where one is visible in FIG. 4A. The protrusions extend through two cut-outs 92, FIG. 3C, arranged on the main housing providing three distinct positions of the protrusions to be placed, each corresponding to a specific mode of function, such as LOCKED, UNLOCKED and INJECTION, as will be explained in detail below. The positions are preferably marked with suitable indications on the main housing for facilitating the proper use of the device. In that respect the mode selector is preferably made of a clear material. The protrusions 90 extend into corresponding recesses 92, FIG. 2A, in the dose actuating sleeve 50 in order to manoeuvre the dose actuating sleeve as will be explained.

The device is intended to function as follows. The injector is received by the patient as shown in FIG. 1, with the needle shield in a retracted position held there by appropriate releasable holding means. The mode selector 88 is positioned with its protrusions in the UNLOCKED position, FIG. 3C. This facilitates for the patient to attach a needle by threading a needle, arranged inside a needle cover 94, onto the threaded neck portion 26 of the container holding housing 14, FIG. 3. An inner end of the needle will thereby penetrate a membrane at the front end of the container, thereby establishing a passage between the needle and the interior of the container. It is also conceivable to omit the releasable holding means whereby the device is delivered with an extended needle shield. When the mode selector is placed in the UNLOCKED position the needle shield can be pushed inside the main housing because of the configuration of the grooves 38 enabling the protrusions 54 to slide between a front and a rear position in the groove, as indicated in FIG. 3D. In this case the needle shield is pushed inside when a needle is attached.

The mode selector is then turned and pushed forward and to the LOCKED position, FIG. 4C, whereby the dose actuating sleeve 50 is turned and moved forward by the spring 58 acting on the dose actuating sleeve 50 which in turn moves the needle shield forward. The protrusions 54 of the dose actuating sleeve are moved in the grooves 38 to a position as shown in FIG. 4D, in which position the protrusions 54 engage with mating ledges 96 on the inner surface of the main housing, thereby locking the needle shield, FIG. 4B. This movement causes the needle cover 94 to be pushed off the needle and the needle shield 34 surrounds the needle in a locked position. The next step, FIGS. 5–7, is to prime the device, i.e. remove all possible air entrained inside the container. The patient thereby turns the dose setting knob 84 until the indication "prime" or any other suitable indication, is visible in the window 70, FIG. 5. The turning of the dose setting knob 84 causes it to move a certain distance X in relation to the main housing 12. The force from the spring 71 between the nut and the dose nut 62 urges the dose nut upwards and because the dose setting knob is moved, the dose nut will rotate along the drive rod 42 and move the distance X because the tongues 75 are in contact with the dose setting knob, thereby creating a distance X between the front end of the first section 64 of the dose nut and the lock nut 46 FIG. 5A. The rotation of the dose nut is also enabled because the mode selector 88 previously has been moved forward to the INJECTION position, FIG. 5C, and thereby the dose actuating sleeve and the lock sleeve 48, whereby the lock sleeve and its splines have been moved out of contact with the splines 65 of the dose nut 62. However the splines of the lock sleeve are in engagement with the splines 24 of the container holding housing 14 and the splines of the nut 46.

In order to initiate priming, FIG. 6A, the mode selector 88 is turned anti-clockwise somewhat in order for the protrusions 54 to move out of contact with the ledges 96 and pulled backwards in the direction of arrow I, whereby the dose actuating sleeve 50 also is pushed backwards due to the protrusions 90 and the needle shield 34 due to its connection with the dose actuating sleeve via the groove 38 and protrusions 54, FIG. 6D. This in turn moves the lock sleeve 48 backwards because its engagement with the dose actuating sleeve until the splines of the lock sleeve are brought out of engagement with the rotationally fixed splines 24 of the container holding housing 14. The lock sleeve 48 is now free to rotate and because of the forwardly directed force of the drive rod spring 78 the drive rod will start to rotate in relation to the fixed threads of the container holding housing 22 in unison with the lock nut 46, the lock sleeve 48 and the dose nut 62. This rotation causes the advance of the drive rod 42, the lock nut, which slides along the drive rod with its protrusions 47 in the longitudinal grooves of the drive rod, and the dose nut until the lock nut abuts the rear end of the dose holding housing and the front end of the first section 64 abuts the lock nut 46, thereby locking the drive rod from rotation, FIG. 7. The rotation of the dose nut enables an indication to be shown in the window 70 that the priming is completed.

The device is now primed and when the mode selector 88 is released it is pushed forward by the spring 58 whereby the protrusions 90 are positioned in the LOCKED position in the cut-out of the main housing, FIG. 11C and the device is locked, FIG. 8. The needle shield 14 is also locked in that the protrusions 54 extending through the recesses 38 of the needle shield are in engagement with ledges 96 arranged on the inside of the main housing 12, FIG. 8B.

In order to perform an injection the required dose has to be set, which is done by turning the mode selector to INJECTION whereby the protrusions 54 of the dose actuating sleeve 50 are positioned as shown by dotted lines in FIG. 10D. The dose setting knob 84 is then turned until the required dose is visible in the window 70, FIG. 9. As with the priming, the turning of the setting knob enables the dose nut 62 to rotate along the drive rod 42 and move a certain distance Y from the lock nut 46. Again the lock sleeve 48 is in a position such that it locks the nut and is at the same time prevented from rotating because of the engagement with the splines 24 of the container holding housing 14, FIG. 9. The device is now pressed against the injection site whereby the needle penetrates the skin. At the same time the needle shield 34 is pushed into the device. Because of the fixed connection between the groove 38 and the protrusions 54, in that the protrusions move to the position shown with unbroken lines in FIG. 10D, the movement of the needle shield causes the dose actuator sleeve 50 to move backwards and thereby also the lock sleeve 48, FIG. 10. When the lock sleeve has moved backwards a certain distance the engagement between the splines of the lock sleeve and the splines 24 of the container holding housing 14 is released and the lock sleeve and thus the drive rod 52 is free to rotate and to be moved forward because of the threaded engagement with the threads 22 of the container holding sleeve. Again the rotation continues until the lock nut 46 comes in contact with the rear end of the container holding housing and the dose nut 62 comes in contact with the lock nut, FIG. 11, whereby the injection is completed. And again the rotation of the dose nut provides for an indication in the window 70 that the injection is completed.

The needle may now be withdrawn from the patient, whereby the needle shield 34, the dose actuating sleeve 50, the lock sleeve 48 and the mode selector 88 are pushed forwards by the force of the spring 58 until the protrusions 90 enter the LOCKED position. The needle shield is now locked in order to prevent accidental needle sticks. During the injection, the dose adjusting means 62 moved forward the distance Y in relation to the dose pusher 72. Thus, upon completion of the injection this distance Y is present between the bottom surface of the third section 68 and the front end surface of the dose pusher, FIG. 11A. When now the dose actuating sleeve and the lock sleeve are moved forward the dose nut is free to rotate along the drive rod until the bottom surface of the of the third section again abuts the front end surface of the dose pusher. This means that the previously set dose becomes the "default" dose for the subsequent injection as the mode selector is positioned in the INJECTION position. Thus, a patient does not have to adjust the dose for each injection unless a different dose is required.

If the last dose is smaller than the preset dose or for that matter a dose the patient is trying to set, this cannot be performed due to the stop means 43 at the end of the drive rod. The stop means prevents the dose nut from rotating any further, whereby the dose quantity that can be delivered is shown in the window 70 when the dose nut has been turned until it abuts the stop means, either when automatically adjusted as described above, or when a patient tries to set a certain dose, thus ensuring that the set dose cannot be larger than the remaining quantity and the actual dose that can be delivered is displayed in the window. However, it is possible to rotate the dose setting knob further, but this action will not affect the dose nut, that thus still will show the dose that can be delivered. It is of course still possible to set a smaller dose than the last preset remaining dose in the container. Also in order to ensure this the length of the drive rod is adjusted to correspond to the stroke of the medicament container.

For a subsequent dose, or for storage, it is necessary and preferable respectively that the used needle is removed and possibly replaced. In order to remove the needle the mode selector is set to UNLOCKED whereby the needle shield can be pushed inside the device as described above in connection with FIG. 3D. The needle cover is pushed into the needle shield and the needle shield is retracted and acts as a guide for the needle cover for obtaining the right position and angle in relation to the needle, thus assuring that the needle does not accidentally penetrate the needle cover. The needle can then be unscrewed from the threaded neck portion. The device can now be stored or be prepared by attaching a new needle to the device, in the same manner as described above. In this respect, and as indicated above, the grooves 38 of the needle shield may have a different design or configuration.

It is of course possible to alter the design of the injecting device according to the invention within the scope of protection. A variant is shown in FIGS. 19A, B comprising a main housing 12' a dose setting knob 84', a window 40' for viewing the container and its content and a window 70' for displaying the set dose or that a dose has been delivered. The interior mechanism is otherwise very similar to the previous embodiment. With this variant the mode selector 88' is placed in the front end of the device. As with the previous selector it can be positioned in different modes of operation (LOCKED, UNLOCKED and INJECTION) enabling the same functions as above and also slidable in the longitudinal direction for attaching, replacing or removing a needle, priming and the like. With this variant the selector also acts as the needle shield so that when placed in INJECTION mode the mode selector/needle shield is pressed against the injection site and thus pressed into the device, thereby actuating the injection in the same way as described above. This variant has the advantage that the mode selector has the dual function of needle cover, thus reducing the number of components of the device. It is also been proven logical for a user to have the mode selector, by which the needle can be attached, the dose primed and the injection initiated, at a location where the needle actually is situated.

A second embodiment will now be described in connection with drawings 13 to 19.

Figure 13:
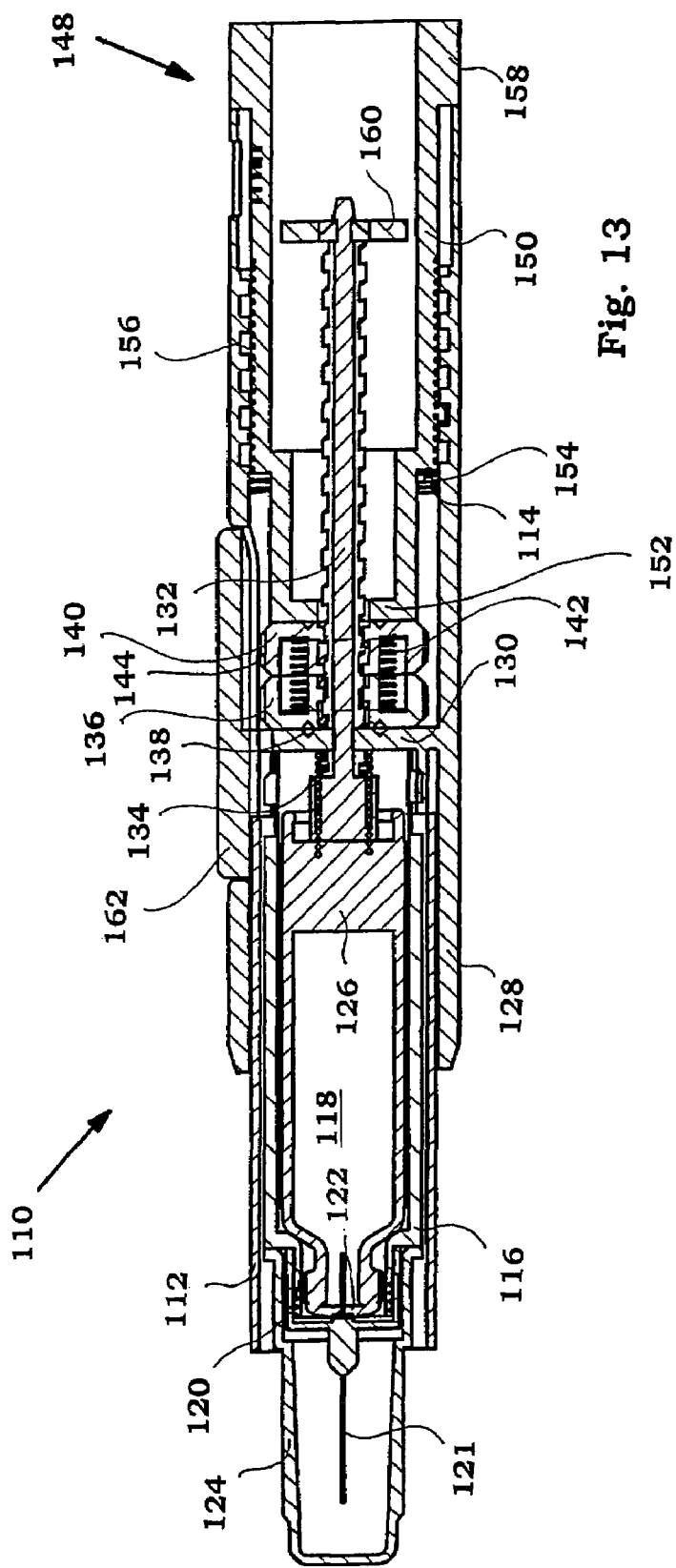
FIG. 13 is a longitudinal cross-sectional view of a second embodiment injector according to the invention.

The second embodiment comprises a needle shield 112 of a generally tubular shape and open at both ends. In FIG. 13 the needle shield is held in a retracted position against the force of a spring not shown. The needle shield surrounds a generally tubular container holding housing 116. Inside the container housing a container 118 is arranged, which contains the medicament to be delivered. The front end of the container housing is arranged with a threaded neck 120 onto which a needle 121 can be threaded. In doing so, the rear end of the needle penetrates an elastic membrane arranged at the end of the container, thereby providing access to the medicament through the needle. A needle cover 124 is further arranged around the needle. The rear end of the medicament container is provided with a piston 126 slidable within the container.

The container housing 16 is attached to a main injector housing 128 of a generally tubular elongated shape. Inside the main housing a wall 130 is arranged. The wall is arranged with a centrally located passage, through which a shaft 132. The shaft is provided with threads. The passage and the shaft are arranged such that the shaft may slide through the passage but is prevented from rotating. The front end of the shaft, to the left in the figures, is abutting the piston of the container. A dose actuation spring 134 is arranged between the piston and the wall and is surrounding the shaft. On the right side of the wall, as seen in the figures, a first nut 136 is threaded onto the threaded shaft and in sliding contact with the wall 130. Friction-reducing means 138 are arranged between the nut and the wall, such as low-friction surfaces or ball bearings. A second nut 140 is also threaded onto the shaft and a compression 142 is arranged between the two nuts in respective recesses. The outer surfaces of the nuts are arranged with a plurality of grooves 144 directed in the longitudinal direction of the injector. These grooves cooperate with protrusions or splines 146 on the inside of the inner end of the needle shield in a manner which will be explained below.

Dose adjusting means 148 is arranged at the right end of the injector. It comprises a generally tubular body 150 extending into the main body. The inner end of the dose body is arranged with a wall 152, which wall is provided with a passage for allowing the threaded shaft 132 to pass through. The spring 114 of the needle shield 112 is resting against a ledge 154 of the dose body. The outer surface of the dose body and the inner surface of the main body are provided with corresponding threads 156 in order to displace the dose body 150 axially in relation to the main body 128 for adjusting the dose quantity. The right-most end of the dose body is provided with a gripping part 158 for rotation of the dose body in relation to the main body. The outer end of the shaft is arranged with a movement limiting washer 160. The injector is further provided with a safety button 162 arranged on the main body and designed with a longitudinally extending protrusion, which protrusion, when pressing the button into the main body, co-acts with the recesses 144 of the nuts 136, 140 in a way which will be described below.

Figure 14:
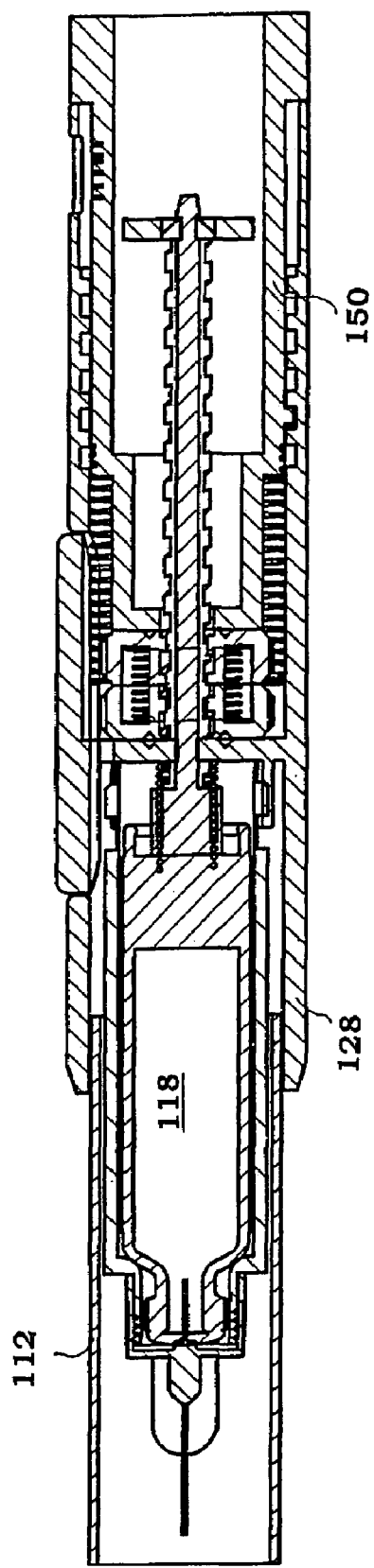

The injector according to the invention is intended to work as follows. When a patient receives a new injector, it is pre-loaded with a medicament container 118. The nuts 136, 140 have been threaded onto the shaft 132 so that the end of the shaft is abutting the piston 126 of the container. Thereby the actuating spring 134 is fully compressed. The user thus do not need to pre-tension the actuating spring before use. The needle shield 112 is further brought to its retracted state. When the patient is to inject a dose he picks a new sterile needle 121, often complete with a safety cap 124, and threads it onto the threaded neck 120 of the container holder 116. The needle shield is then released and the needle shield spring urges the needle shield forward, to the left in the figures. This movement may causes the end of the needle shield to push off the needle cover, FIG. 14, due to the design of the needle cover. The next step is to set the dose. The dose body 150 is then turned by the gripping part 158 to a certain dose quantity position, FIG. 15. In order for the patient to adjust the dose body, the injector may be provided with display means indicating the adjusted dose. This may for example be done by a scale marked on the main body adjacent the gripping part and an arrow or mark on the gripping part. The gripping part may then be turned until the arrow is opposite the desired dose quantity.

The turning of the gripping part and thus the dose body causes the dose body to move axially in relation to the main body due to the threads between the two, arrow 170, FIG. 15, a certain distance a. Due to the spring 142 or torsion between the nuts 136, 140 the second nut 140 is threaded along the shaft the same distance a as the dose body has moved. The force of the spring reduces the play between the parts, enhancing the precision of the device. The first nut 136 is prevented from rotating due to the protrusion 172 on the needle shield 112, which is in contact with the grooves on the periphery of the nut, FIG. 15a. The injector is now ready for injection.

Figures 16A, 16B:
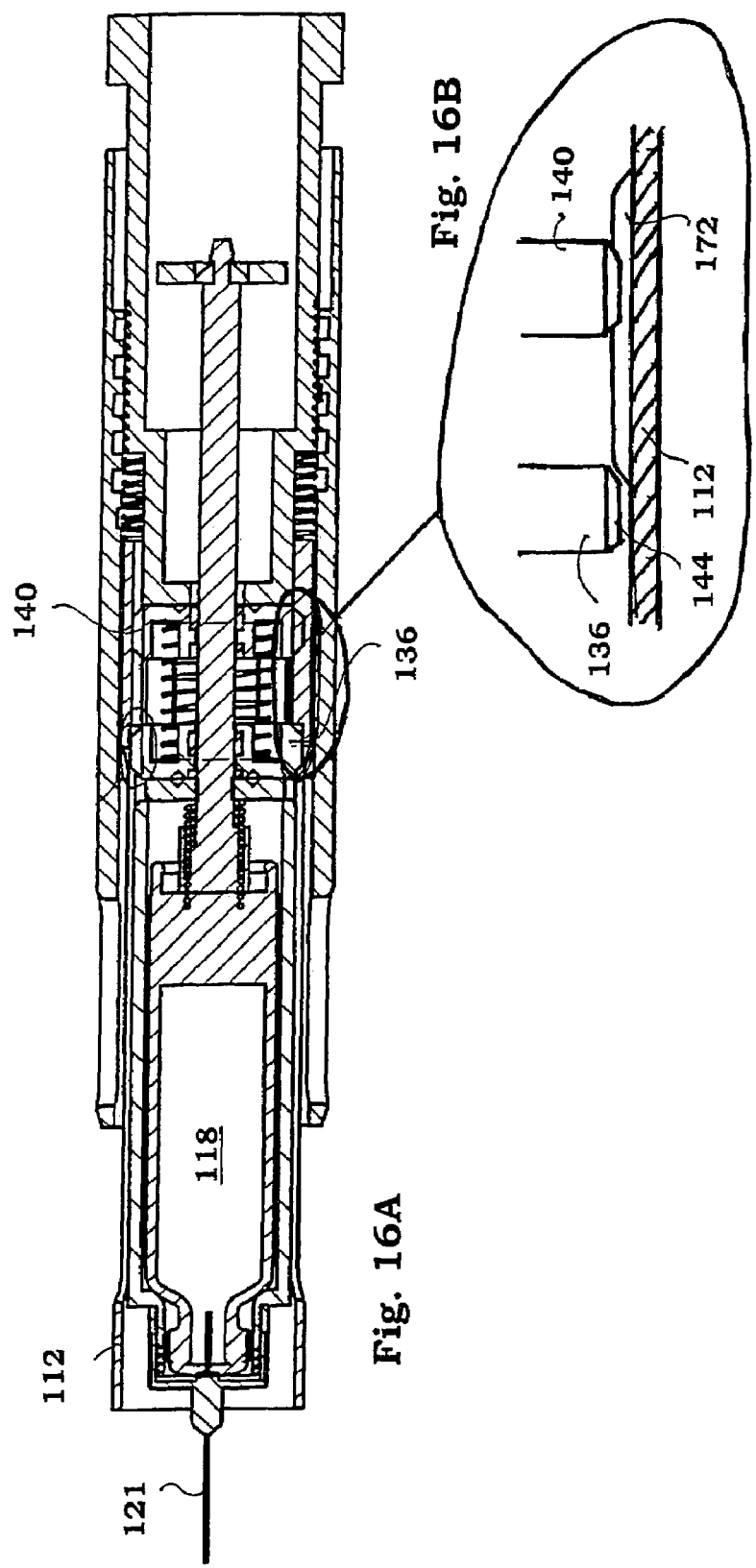

This is done by pushing the outer end of the needle shield 112 against the injection site, pushes the needle shield into the injector against the spring force, thereby penetrating the skin with the needle, FIG. 16. The force from the needle shield aids in stretching the skin part to be penetrated. The pushing of the needle shield into the main body causes the protrusion 172 of the needle shield 112 to come out of contact with the grooves 144 of the first nut, FIG. 16b. Because the first nut 136 now is free to rotate and because of the force from the actuating spring and the low friction between the first nut 136 and the wall 130 because of the low-friction means 138, the first nut will rotate. The rotation causes the shaft to be moved axially to the left in the figures due to the threads between the first nut 136 and the shaft 132. The second nut is now locked by the protrusion 172 of the needle cover 112, FIG. 16b. The axial movement of the shaft pushes the piston 126 into the container so that medicament is injected into the patient through the needle 121. The axial movement continues until the second nut 140 comes in contact with the first nut 136 under compression of the spring 142 between the nuts where the second nut 140 is prevented from rotating by the protrusion 172 of the needle shield engaging the grooves of the second nut, FIG. 17. It is to be noted that the spring 142 between the two nuts is much weaker than the force from the actuation spring.

Figure 18:
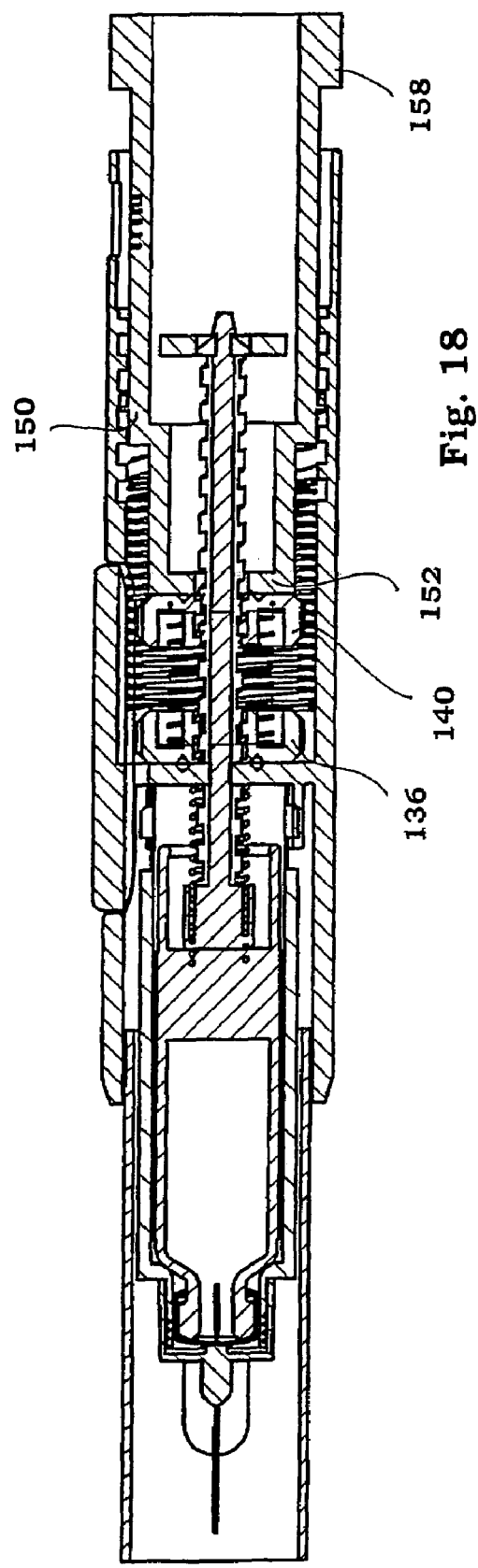

The injection is now completed and the needle is withdrawn from the patient. The spring 114 of the needle shield then pushes needle shield out of the injector whereby the second nut 140 again is released and is threaded along the shaft until it comes in contact with the wall 152 of the dose body 50. The injector is thus again ready for use, FIG. 18. As can be understood from the foregoing and from the figures the subsequent dose will be of the same quantity if no adjustment is made of the dose body. If the same dose quantity is to be delivered repeatedly the patient does not have to make any adjustments whatsoever. It is to be noted that the increments of the dose size and precision of the of the injector is very much determined by the pitch of the threads and number of grooves.

In order not to activate the injector because the needle shield is pushed back, the patient presses a mode state button/means 162. Thereby the protrusion of the button engages the grooves of the first nut and prevents it from rotating even if the protrusion of the needle shield comes out of contact with the grooves of the first nut. When the patient is to take a subsequent dose the needle has to be replaced with a new, sterile, needle. He therefore pushes the needle shield back to be able to replace the needle.

When the container is nearly empty, the locking washer 160 is close to the dose body wall 152 it limits how much the shaft is able to move in the subsequent injection. It is then impossible to adjust the dose body further than the remaining dose because adjustment of the dose body, ie axial displacement, will cause the wall of the dose body to come in contact with the locking washer. This indicates to the patient that the medicament container is almost empty and/or may not be able to deliver the required dose of medicament. It is conceivable that the end of doses locks the needle shield and the safety button so that the injector can safely be discarded.

In some instances before the first injection the injector has to be primed, ie to empty the container of possible air trapped inside. Then the second step after connecting a needle is to adjust the dose body to a priming position, thereby moving the dose body and the second nut a certain distance axially, in the same manner as described in connection with injections. As also described earlier, when the needle shield is nearly fully pushed into the injector, the protrusion of the needle shield is moved out of contact with the grooves of the first nut. It is thereby free to rotate and to be threaded along the shaft due to the force of the compression spring. The shaft is thus moved axially, pushing the piston further into the container whereby entrapped air and medicament is ejected through the needle, until the second nut comes into contact again with the first nut. The needle shield is now released and returns to its extended state. This causes the second nut to be released whereby it is threaded along the shaft until it comes in contact with the wall of the dose body.

The needle shield may also be provided with locking means to lock it in the extended position in order to minimize the risk of accidental needle-sticks. The mode selector means may further be provided with release means for releasing the locking of the needle shield for an injection or for replacing the needle. It may also be provided with three different settings; lock, where the injector and needle shield is locked; load, where it is possible to change needle without the risk of firing the injector; and dose, where the injector is ready for injection as described above. In this context the needle shield may be in two parts, a lower and an upper part, and that the lower part is locked in the extended state after injection and withdrawal of the injector, and that it requires a twist or turning action in order to be released and to co-act with the upper part as described above.

It is to be understood that the invention as described above and shown in the drawings is a non-limiting example and that the invention is defined by the patent claims. Thus, several parts of the described injector may be replaced with other part with the same or similar function as will be readily appreciated by the skilled person.

What is claimed is:

1. Injection device, comprising:
   an elongated body, including a container with medicament,
   a connector for connecting a needle to the container,
   an actuator capable of injecting a dose of the medicament upon activation,
   said actuator comprising a plunger rod connected to said container, an actuating spring arranged to said plunger rod and capable of pushing said plunger rod into said container for expelling the medicament through said needle,
   an activator capable of releasing said plunger rod from a position where the actuating spring is tensioned, and
   a needle shield arranged to said body and slidable between an extended and a retracted position in relation to said body, wherein,
   said needle shield is designed and arranged such that, upon penetration of the needle into a patient, when moved or pushed towards its retracted position, it acts on said activator, which in turn releases said plunger rod for injecting a dose.

2. Injection device according to claim 1, further comprising a dose setting part capable of setting the dose to be injected.

3. Injection device according to claim 2, wherein the dose setting part is designed and arranged such that a set dose will become the subsequent dose if the dose setting part is not adjusted, by e.g. the user.

4. Injection device according to claim 2, wherein the dose setting part is arranged with a stop part preventing a set dose from exceeding a dose remaining in the medicament container.

5. Injection device according to claim 2, wherein the dose setting part comprises at least one threaded nut that is continuously pressed away from its stop surface, thus eliminating mechanical play.

6. Injection device according to claim 1, further comprising a primer for priming the injector before the first injection.

7. Injection device according to claim 1, wherein the priming resets the device for a subsequent dose delivery.

8. Injection device according to claim 6, wherein the primer is comprised of the dose setting part.

9. Injection device according to claim 6, wherein the dose setting part and the primer are separate parts.

10. Injection device according to claim 3, wherein the dose setting part is arranged with a stop part preventing a set dose from exceeding a dose remaining in the medicament container.

11. Injection device according to claim 3, wherein the dose setting part comprises at least one threaded nut that is continuously pressed away from its stop surface, thus eliminating mechanical play.

12. Injection device according to claim 4, wherein the dose setting of part comprises at least one threaded nut that is continuously pressed away from its stop surface, thus eliminating mechanical play.

13. Injection device according to claim 7, wherein the primer comprises the dose setting part.

14. Injection device according to claim 7, wherein the does setting part and primer are separate parts.

15. Injection device, comprising:
    an elongated body including a container with medicament;
    a connector for connecting a needle to the container;
    an actuator configured to inject a dose of the medicament upon actuator activation,
    said actuator comprising a plunger rod connected to said container, an actuating spring arranged to said plunger rod and configured to push said plunger rod into said container for expelling the medicament through a connected needle;
    an activator configured to release said plunger rod from a position where the actuating spring is tensioned; and
    a needle shield arranged to said body and slidable between an extended and a retracted position in relation to said body, wherein,
    said needle shield configured so that upon penetration of the needle into a patient, when moved or pushed towards the retracted position, the needle shield acts on said activator, which activator in turn releases said plunger rod for injecting the dose.

16. Injection device, comprising:
    an elongated body including a container with medicament;
    a connector for connecting a needle to the container;
    an actuator configured to inject a dose of the medicament upon actuator activation,
    said actuator comprising a plunger rod connected to said container, an actuating spring arranged to said plunger rod and configured to push said plunger rod into said container for expelling the medicament through a connected needle;
    an activator configured to release said plunger rod from a position where the actuating spring is tensioned; and
    a needle shield arranged to said body and slidable between an extended and a retracted position in relation to said body so that injection of the does is initiated by the needle shield releasing the plunger rod when moved a certain distance, wherein,
    said needle shield configured so that upon penetration of the needle into a patient, when moved or pushed towards the retracted position, the needle shield acts on said activator, which activator in turn releases said plunger rod for injecting the dose.

* * * * *